United States Patent [19]

Hackler et al.

[11] Patent Number: 5,727,498

[45] Date of Patent: Mar. 17, 1998

[54] RETRACTABLE VISUAL INDICATOR ASSEMBLY

[75] Inventors: George R. Hackler; Ronald J. Gamboa; Victor Dominquez, all of Las Cruces, N. Mex.

[73] Assignee: The United States of America as represented by the Administrator of the National Aeronautics and Space Administration, Washington, D.C.

[21] Appl. No.: 613,737

[22] Filed: Feb. 13, 1996

[51] Int. Cl.⁶ .................................................. G01N 31/22
[52] U.S. Cl. ................. 116/206; 116/276; 116/DIG. 25; 73/866.5
[58] Field of Search ................................ 55/274, DIG. 34; 73/31.03, 866.5; 116/206, 276, DIG. 25; 422/59, 86, 87

[56] References Cited

U.S. PATENT DOCUMENTS

| | | | |
|---|---|---|---|
| 1,813,991 | 7/1931 | Eaton . | |
| 3,200,387 | 8/1965 | Loscher | 55/274 |
| 3,296,854 | 1/1967 | Morgan | 116/276 X |
| 3,736,899 | 6/1973 | Manske | 116/70 |
| 4,315,890 | 2/1982 | Tamers | 422/86 X |
| 4,530,706 | 7/1985 | Jones | 55/275 |
| 4,684,380 | 8/1987 | Leichnitz | 55/274 |
| 4,712,505 | 12/1987 | Wainwright | 116/227 |
| 4,919,892 | 4/1990 | Plumb | 422/58 |
| 4,926,704 | 5/1990 | Survil et al. | 73/866.5 |
| 5,128,106 | 7/1992 | Buschmann et al. | 422/119 |

*Primary Examiner*—William A. Cuchlinski, Jr.
*Assistant Examiner*—Willie Morris Worth
*Attorney, Agent, or Firm*—James M. Cate

[57] ABSTRACT

A retractable indicator assembly 10 may be mounted on a container C which transmits air through the container and removes deleterious gases with an activated charcoal medium M in the container. An elongate indicator housing 12 has a chamber 20 therein. A male adaptor 14 has external threads 16 for sealing engagement with the container. A plug 40 is provided at the upper end of the housing 12. Housing 12 includes a transparent wall portion 28 for viewing at least a portion of the chamber 20. A litmus indicator 42 is moveable by a retractable rod 54 from a retracted position within the container to an extended position within the chamber 20 of the housing 12. An outer housing 64 is secured to the upper end of the rod 54, and protects the indicator housing 12 while the litmus indicator 42 is in its normally retracted position. The assembly may be manually manipulated between its extended position wherein the litmus indicator may be viewed through the transparent wall 28 of the indicator housing 12, and a retracted position wherein the outer housing 64 encloses the indicator housing 12 and engages the exterior of the container C.

20 Claims, 1 Drawing Sheet

RETRACTABLE VISUAL INDICATOR ASSEMBLY

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The present invention relates to a visual sensor for determining contamination of fluid within or downstream from a filter. More particularly, this invention relates to a retractable visual indicator for accurately and safely determining depletion of an activated carbon filter medium without allowing air to escape from the system.

BACKGROUND OF THE INVENTION

Barrels or similar containers housing an activated carbon filter media are commonly used to filter air. In a typical application, the barrel will have an air inlet and an air outlet, and is fluidly provided upstream from a room or chamber which houses personnel. The air transmitted through the barrel is thus exposed to and filtered by the charcoal medium to remove organic vapor or hazardous gases from the air. After an extended period of exposure, the activated carbon filter media will become exhausted or saturated, and must be replaced. It is thus important to periodically check the quality of air within or downstream from the barrel, preferably at a location within the barrel and adjacent the air outlet of the barrel, in order to ensure that the filtering media will be timely changed.

Visual indicators for monitoring gases within a barrel or other container may contain a litmus material which changes color in response to volatile or hazardous gases. The litmus material may, for example, turn black when exposed to a level of organic vapor within the air which is potentially dangerous or harmful to humans. One type of litmus material sensor used to periodically monitor air within a barrel housing a charcoal material filter is manufactured by TIGG Corp. The TIGG sensor is mounted on the barrel with the litmus material sensor being in a fluid communication with the interior of the barrel, yet exterior of the barrel itself. While this type of sensor may be readily checked to determine if the litmus material is changing color, the sensor is slow to respond to changes in the depletion of the charcoal material since there is little exchange of air between the interior of the sensor and the interior of the barrel. Also, this type of sensor may become easily damaged and thus leak since the sensor remains continuously exterior of the barrel. A leak in the sensor will thus allow the litmus material to be exposed to external gases which are not transmitted through the barrel, thereby affecting the reliability of the sensor.

Another type of visual indicator which has been used to monitor the saturation of an activated carbon filter media in a barrel is manufactured by Cameron-Yakimi. This unit is designed to be placed inside the barrel so that the litmus material is exposed to the gases being transmitted through the barrel. The indicator is not, however, visible while gases are being transmitted through the barrel. Gas transmission through the barrel must therefore be periodically terminated, the barrel opened, the indicator checked, and the barrel then either resealed or the filter media changed.

U.S. Pat. No. 1,813,911 discloses an indicating device designed for testing the atmosphere within a sealed tank. The device includes articulated, pivotable arm which translates an indicator rod which, in one position, projects upwardly within a transparent tube mounted above the chamber in the tank. The device includes a container with the chamber which may be charged with phosphorous or another deoxidizing agent which absorbs oxygen from the surrounding air. When oxygen is absorbed, the weight of the material within the container increases. When a predetermined weight is reached, the lever arm is rotated until a counter-weight engages a stop, which moves the rod within the transparent tube. The sensing unit does not rely upon the changing color of a litmus material to detect the presence of gases, and is not suitable for determining the exhaustion of an activated carbon material within a barrel, as described above.

U.S. Pat. No. 4,712,505 discloses a sensor for indicating the presence of hazardous liquids or water within a storage tank. The sensor assembly includes an indicator unit which is provided exterior of the tank, and has a transparent window through which the position of a translatable marker may be observed. The marker is moved by a control cable which is connected to a sensing element. The sensing element remains continually within the chamber. The sensing element moves relative to an anchor, thereby causing the cable to move the marker when the sensing element is exposed to a hazardous liquid or water.

U.S. Pat. No. 3,736,899 discloses a pressure change indicator which is responsive to internal pressure within a vessel. U.S. Pat. No. 5,128,106 discloses an oxygen detector positioned within the outer envelope of an electric lamp for sensing a slow leak of oxygen into the lamp cavity.

While the prior art discloses sensors which utilize litmus material for determining the depletion of an activated carbon filter media within a barrel, the prior art does not disclose a reliable visual indicator for accurately and safely periodically checking the depletion of the filter material in the barrel. The disadvantages of the prior art are overcome by the present invention, and an improved visual indicator is hereinafter disclosed for accurately and safely checking the depletion of an activated carbon filter media within a barrel or other container.

SUMMARY OF THE INVENTION

The retractable visual indicator assembly according to the present invention is adapted to be mounted on a barrel or other container which houses a filter media, such as activated carbon. The indicator assembly may provide a visual indication of the presence of an undesirable gaseous material within the barrel or container. The visual indicator assembly includes an elongated transparent housing with its interior in fluid communication with the interior of the barrel through an opening in the wall of the barrel. A test probe includes a gas-sensitive litmus material which changes color when exposed to an organic or hazardous gas within the barrel. The retractable test probe is translatable with respect to the transparent housing from a retracted position within the interior of the barrel for exposure to the gases, and an extended position wherein the test probe is positioned within the transparent housing.

During normal operation when gases are passed through the barrel, the test probe is left in its retracted position so that the litmus material is continually exposed to gases within the barrel. The indicator assembly is periodically visually checked to ensure that the filtering material is operating satisfactorily by withdrawing the test probe from the barrel until the test probe is within the transparent housing, so that the litmus material may be readily observed. The transparent housing is sealingly fitted to the vessel for preventing leakage of any gas from the barrel during retraction and extension of the test probe. In a preferred embodiment, the visual indicator assembly may be used to detect a volatile, organic vapor which may have collected over a bed of activated carbon, thereby indicating exhaustion of the activated carbon filtering media.

It is an object of the present invention to provide an improved visual indicator for sensing the quality of undesirable gases within a barrel or other chamber which houses a filter media, thereby providing an indication of the depletion or exhaustion of the filtering media. It is a related object of the invention to provide a visual indicator suitable for use with a barrel which houses an activated charcoal filter media, wherein the indicator does not allow for the escape of gases from the barrel. Still another object of the invention is to provide a visual indicator with a sensor which is retractable from a normally retracted position within the barrel for accurately responding to the quality of gases within the barrel and an extended position wherein the sensor is exterior of the barrel and may be visually observed.

It is a feature of the present invention that the visual indicator utilizes a sensor which includes a litmus material which is color-responsive to selected gases within the barrel or filter material container. The sensor provides a direct indication of the presence of volatile or hazardous gases within the barrel, since the sensor is normally directly in the flow stream of air passing through the barrel. A related feature of the invention is that the visual indicator is able to easily and reliably detect depletion of the filtering media within the barrel, thereby providing an accurate indication of potentially harmful gases being transmitted through the barrel.

It is a significant advantage of the invention that the barrel or container containing the activated carbon filter media need not be opened in order to inspect depletion of the filtering media. It is the further advantage of the invention that the indicator allows an operator to easily withdraw the sensor from the interior of the barrel, view the sensor, and reinsert the sensor within the interior of the barrel.

These and further objects, features, and advantages of the present invention will become apparent from the following description, wherein reference is made to the figure in the accompanying drawing.

DETAILED DESCRIPTION OF PREFERRED EMBODIMENTS

Figure 1:
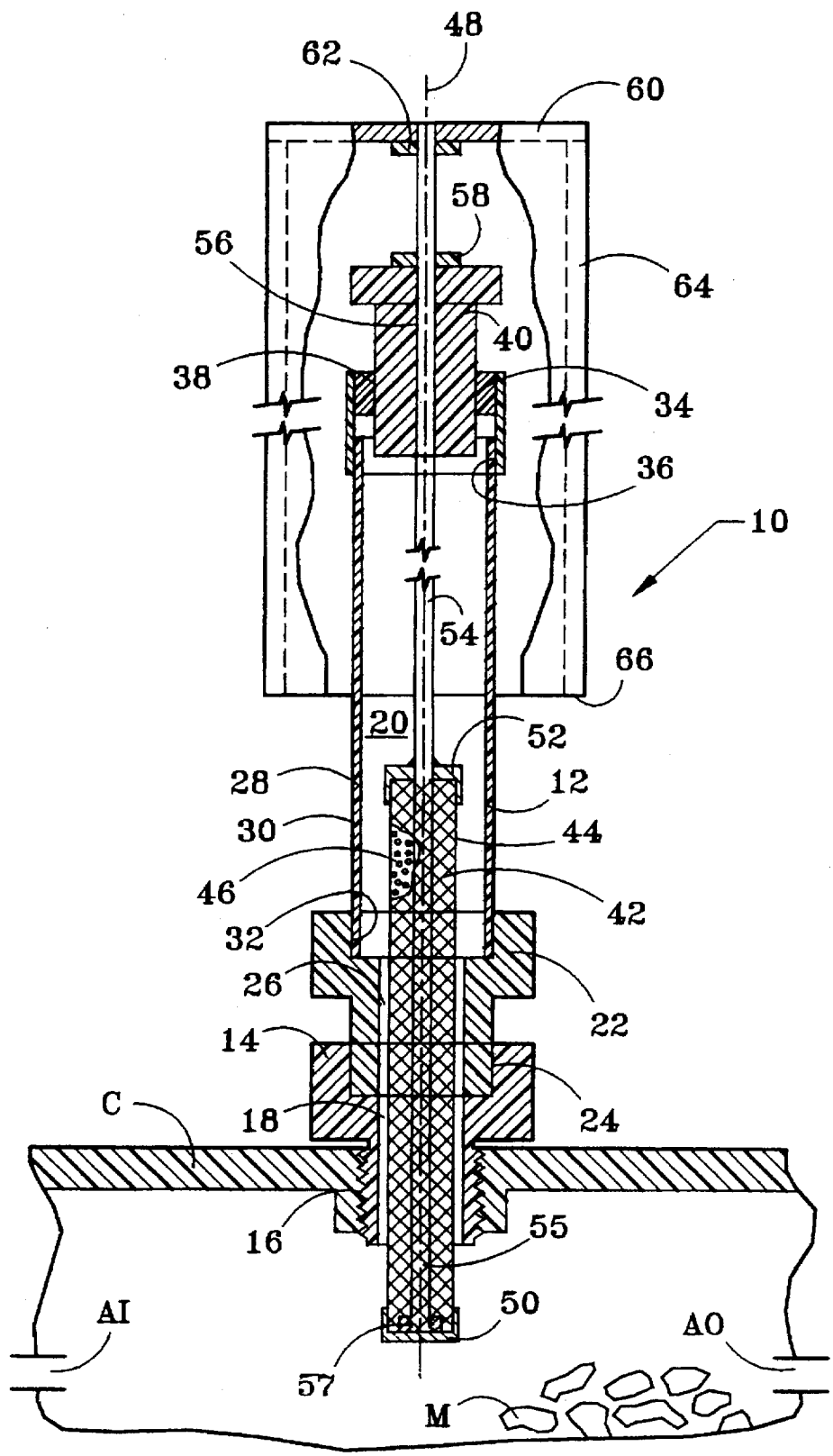
FIG. 1 is side view, partial and cross-sectioned, of a suitable indicator according to the present invention mounted on a barrel. The indicator is shown in its extended position for viewing the litmus material. The indicator may be moved to a retracted position by lowering the outer protective housing to engage the barrel.

FIG. 1 depicts one embodiment of an indicator assembly 10 according to the present invention mounted on a barrel or other container C. Those skilled in the art will appreciate that the container conventionally has an air inlet AI and an air outlet AO for transmitting air through the container C. The interior of the container C is substantially filled with an activated charcoal filtering media M which removes organic vapors from the air passing through the container, thereby purifying the air so that it is suitable for discharge to a room containing personnel. It should be understood that the filtering media within the container C will be selected based upon the likely deleterious gases which might be transmitted with the air into the container, and that any suitable filtering media or several types of filtering media may be used according to this invention. As explained below, the indicator assembly may be periodically checked to provide an indication of the deleterious gases within the container, thereby ensuring the timely replacement of an exhausted or otherwise malfunctioning filtering media.

The indicator assembly 10 comprises an elongate indicator housing 12 which is securely mounted on the exterior of container C. A male adaptor 14 includes external threads 16 for threaded engagement with a threaded aperture in the wall of the container C. The indicator is sealingly engaged with the container. In the present embodiment, and as shown in FIG. 1, sealing engagement is provided by the threaded engagement of the external threads 16 of the male adapter 14 and the threaded aperture in the container wall. The male adaptor 14 also includes an axial passageway 18 therethrough which provides fluid communication between the interior of the container C and the chamber 20 within the housing 12. A reducing coupling 22 has an external cylindrical surface 24 for planar engagement with a corresponding internal cylindrical surface on the male adaptor 14, and has a similar axial passageway 26 therein for fluid communication between the interior of the container C and the chamber 20. The cylindrical surfaces of male adaptor 14 and reducing coupling 22 may be fixed together and sealed by a suitable adhesive.

At least a portion of the indicator housing 12 has a transparent wall 28 for allowing an operator to view at least a portion of the chamber 20 in the indicator housing 12. Preferably at least a portion of the indicator housing 12 includes a transparent sleeve 30 which may be manufactured from a clear polyvinylchloride (PVC) material. The lower end of the sleeve 30 may be fitted within a cylindrical aperture 32 within the reducing coupling 22, and may be sealed therewith by a suitable adhesive or sealant. A female adaptor 34 may be fitted over the upper end of the transparent sleeve 30, with the cylindrical internal surface 36 of the female adaptor similarly sealed with an exterior surface of the sleeve 30. An internal cylindrical surface on the female adaptor 34 may be fitted to a corresponding external cylindrical surface 38 on plug 40, thereby forming a plugged upper end of the indicator housing 12. The mated cylindrical surfaces on the female adapter 34 and the plug 40 may again be sealed by an adhesive.

A litmus indicator 42 comprises an exterior screen 44 which houses litmus granules 46 therein. The litmus indicator is an elongate member which is movable between a retracted position and an extended position along a central axis 48 of the assembly 10, as explained below. The lower end of the litmus indicator 42 may receive a stainless steel cap 50, while the upper end of the indicator receives a similar cap 52. The diameter of both the lower cap 50 and the upper cap 52 may be sized such that the caps may pass through the passageways 18 and 26 in the male adapter 14 and the reducing coupling 22, respectively, when the litmus indicator is moved to its extended or retracted position.

An elongate rod 54 is provided as a retracting member for moving the litmus indicator 42 between its extended and retracted positions. The rod 54 may be welded to the upper stainless steel cap 52. The rod 54 passes through a cylindrical aperture 56 provided in the plug 40. A gasket or other suitable seal 58 provides dynamic sealing engagement between the plug 40 and the rod 54 during reciprocation of the litmus indicator. The upper end of the rod 54 may pass through a central hole provided in an upper plate 60. A gasket or other suitable seal 62 may be provided about the rod 54 and secured to the plate 60. The indicator assembly 10 is normally in the retracted position, as explained subsequently. When in the retracted position, the seal 62 engages the seal 58 to provide a redundant sealing capability. An exterior housing 64, which may consist of a stainless steel heavy wall pipe, may be welded to the periphery of the upper plate 60. The housing 64 provides physical protection to the indicator housing, particularly when in the retracted position. The housing 64 also protects the litmus material 46 from exposure to sunlight except when the indicator assembly is periodically extended, thereby prolonging the life of the litmus material. When the indicator assembly is in its retracted position, a portion of the weight of housing 64 may be applied to the plug 40 through the seals 62 and 58 sandwiched therebetween, thereby enhancing the effectiveness and life of the seals.

The lower portion 55 of the rod 54 may extend downward through the litmus indicator 42. Lowermost threads 57 on the lower portion 55 of the rod may mate with similar threads on the lower cap 50. If the litmus material 46 needs repladng, the cap 50 may be unthreaded from the lower portion 55 of the rod, the litmus material 46 replaced, and the cap 50 rethreaded on the rod.

During normal operation with air being transmitted through the container or dream C, the indicator assembly 10 is in its retracted position. In that position, the lower planar surface 66 of the outer housing 64 is in engagement with the container C, thereby providing a covering extending from the surface of the container C to above the indicator housing 12. In the retracted position, the upper plate 60 will thus be axially spaced a selected distance above the plug 40 to slightly compress the seals 58 and 60, as explained above. The rod 54 extends downward through the plug 40, through the entirety of the transparent sleeve 30, and through the reducing coupling 22. When in the retracted position, the upper cap 52 may be positioned within the male adaptor 14, or alternatively may be positioned below the male adaptor and within the interior of the container C. It should be understood that, while in the retracted position, substantially the entirety of the elongate litmus indicator 42 is thus positioned within the container C so that the litmus indicator is within the flow path of the air being transmitted through the barrel or container C.

An operator may periodically check the depletion of the filter media by grasping and manually raising the outer housing 64, thereby moving both the rod 54 and the litmus indicator 42 toward its extended position. While in the extended position, at least a portion of the litmus indicator 42 will thus be visible through the transparent wall 28 of the indicator housing. According to preferred procedure, the operator may raise the outer housing 64 until the upper cap 52 is positioned just below the plug 40, and which time substantially the entirety of the litmus indicator 42 will be positioned within the interior chamber 20 of the transparent sleeve 30, and thus may be visually seen by the operator. If the litmus material 46 within the indicator 42 has not changed color or shows only a slight change in color, the operator may lower the outer housing 64 to its retracted position, thereby bringing the lower surface 66 into engagement with the barrel or container C. If a substantial portion of the litmus material has changed color, thereby indicating the presence of a deleterious gas within the container C and thus the depletion or exhaustion of the activated carbon filtering media M, the indicator assembly 10 may be unthreaded from the used container, a new container with fresh carbon filtering media placed on-line, and the indicator assembly 10 threaded on the new container. If the litmus material 46 has changed sufficiently such that its continued reliability as a visual indicator is in question, the litmus material 46 may be replaced or a new or re-conditioned litmus indicator installed on the new container. Once installed, the assembly 10 allows the litmus indicator to thereafter be easily withdrawn, viewed by an operator, then reinserted within the barrel or container without venting any air from the interior of the barrel.

According to one embodiment, the male adaptor 14, the reducing coupling 22, the female adaptor 34, and the plug 40 may each be fabricated from a suitable plastic material. Those skilled in the art will readily appreciate that the number of components in the assembly 10 may be reduced by combining the functions of the male adaptor 14 and the reducing coupling 22. The arrangement illustrated in FIG. 1 is preferred since a plastic male adaptor and plastic reducing coupling are readily available components, and since the sleeve 30 may be easily sealed with a plastic reducing coupling 22. Similarly, the purpose served by the female adaptor 34 and the plug 40 may be combined. A number of suitable seals may be used to seal between the rod 54 and the plug 40.

By positioning the litmus indicator 42 within the barrel when in its normally retracted position, the indicator is continuously exposed to the flow of gases being transmitted through the barrel, thereby allowing the indicator to promptly and accurately detect depletion of the filter media. When raised to its extended position, an operator may visually see the litmus indicator without allowing fluid to escape from either the barrel or the assembly 10. As previously indicated, various types of filter media may be placed within the barrel for filtering contaminants from the air, and the selected litmus granules within the indicator will be a function of the anticipated contaminants within the air stream.

The indicator assembly as described herein is particularly well suited for monitoring the depletion of an activated carbon filter media within a barrel or container intended for transmitting air through the container. The indicator assembly may be used, however, for providing an indication of a deleterious gas passing through various types of containers designed for transmitting various types of fluids through the containers. The filter media thus may be activated charcoal or activated carbon, but may also be other types of filtering media commonly designed to remove harmful gases from a flow stream.

Various modifications to the retractable indicator assembly will be apparent from the above description of the preferred embodiments. While the invention has thus been described in detail for these embodiments, it should be understood that this explanation is for illustration, and that the invention is not limited to the disclosed embodiments. Modifications to the described structure and to the method of forming retractable indicator assembly are thus contemplated and may be made without departing from the spirit of the invention, which is defined by the claims.

What is claimed is:

1. An indicator assembly for mounting on a container housing fluid in the interior of the container, the indicator assembly providing an indication of deleterious gases within the interior of the container, the indicator assembly comprising:

an indicator housing adapted to be mounted on the exterior of the container and having a housing chamber therein;

the indicator housing having a lower end for sealing engagement with the container and an upper plugged end, the lower end having an opening, the indicator housing having a passageway extending therethrough and communicating with the opening, and adapted to communicate through the opening with the housing chamber, the indicator housing including a transparent wall portion for viewing at least a portion of the housing chamber;

a litmus indicator movable between a retracted position within the container and an extended position within the housing chamber, the litmus indicator including a chemically responsive litmus material for changing color in response to the deleterious gases; and a retractable member interconnected with the litmus indicator and extending through the upper plugged end of the indicator housing for moving the litmus indicator between the retracted position and the extended position.

2. The indicator assembly as defined in claim 1, wherein the lower end of the indicator housing includes threads for threaded engagement with a threaded aperture within a wall of the container.

3. The indicator assembly as defined in claim 1, wherein the indicator housing includes an elongate transparent sleeve including the transparent wall portion and defining a portion of the chamber within the indicator housing.

4. The indicator assembly as defined in claim 1, wherein the retractable member includes an elongate rod fixed to the litmus indicator and sealingly extending through the plugged end of the indicator housing.

5. The indicator assembly as defined in claim 4, further comprising:

an outer housing secured to an upper end of the elongate rod for protecting the elongate indicator housing; and a lower surface on the outer housing engages the container to position the litmus indicator within the container when in the retracted position.

6. The indicator assembly as defined in claim 5, wherein the outer housing includes an opaque tubular member and an upper plate secured to both the rod and the opaque tubular member.

7. An indicator assembly for mounting on a container having an air input port and an air discharge port for passing air through the interior of the container, the indicator assembly providing an indication of deleterious gases within the interior of the container, the indicator assembly comprising:

a threaded fitting having external threads for threaded engagement with a threaded aperture within a wall of the container, the threaded fitting having a passageway therethrough;

an elongate indicator housing having a lower end adapted to be sealingly engaged with the threaded fitting and an upper plugged end, the indicator assembly having a housing chamber within the indicator housing and having an opening communicating between the housing chamber and the passageway of the threaded fitting, the passageway providing fluid communication with the interior of the container, the indicator housing including a transparent wall portion for viewing at least a portion of the housing chamber;

a litmus indicator movable within the passageway between a retracted position within the container and an extended position within the housing chamber, the litmus indicator including a chemically responsive litmus material for changing color in response to the deleterious gases;

a retractable rod interconnected with the litmus indicator and extending through the upper plugged end of the indicator housing, the retractable rod comprising means for moving the litmus indicator between the retracted position and the extended position; and a seal for providing sealing and sliding association between the retractable rod and the plugged end of the indicator housing.

8. The indicator assembly as defined in claim 7, wherein the indicator housing includes an elongate transparent sleeve including the transparent wall portion and defining a portion of the chamber within the indicator housing.

9. The indicator assembly as defined in claim 7, further comprising:

an outer housing secured to an upper end of the retractable rod for protecting the elongate indicator housing; and a lower surface on the outer housing engages the container to position the litmus indicator within the container when in the retracted position.

10. The indicator assembly as defined in claim 9, wherein the outer housing includes an opaque tubular member and an upper plate secured to both the rod and the opaque tubular member.

11. The indicator assembly as defined in claim 9, further comprising:

the outer housing having an axial length greater than an axial length of the indicator housing.

12. The indicator assembly as defined in claim 7, further comprising:

the litmus indicator including an elongate exterior screen having litmus granules therein.

13. An indicator assembly for mounting on a container transmitting air through the interior of the container, the indicator assembly providing an indication of deleterious gases within the interior of the container, the indicator assembly comprising:

an elongate indicator housing mounted on the exterior of the container and having a housing chamber therein;

the indicator housing having a lower end for sealing engagement with the container, said lower end including a passageway therethrough for communicating between the housing chamber with the interior of the container, the indicator housing including a transparent wall portion for viewing at least a portion of the housing chamber and an upper plugged end;

a litmus indicator movable within the passageway between a retracted position within the container and an extended position within the housing chamber, the litmus indicator including a chemically responsive litmus material for changing color in response to the deleterious gases;

an elongate retractable member interconnected with the litmus indicator and extending through the upper plugged end of the indicator housing for moving the litmus indicator between the retracted position and the extended position; and an outer housing secured to an upper end of the elongate retractable member for protecting the elongate indicator housing, a lower surface on the outer housing engaging the container when the litmus indicator is in the retracted position.

14. The indicator assembly as defined in claim 13, wherein the indicator housing includes an elongate transparent sleeve including the transparent wall portion and defining a portion of the chamber within the indicator housing.

15. The indicator housing as defined in claim 13, wherein the outer housing includes an opaque tubular member and an upper plate secured to both the elongate retractable member and the tubular member.

16. The indicator assembly as defined in claim 13, wherein the retractable member includes an elongate rod fixed at its lower end to the litmus indicator and extending through the plugged end of the indicator housing.

17. The indicator assembly as defined in claim 16, further comprising:

a seal for dynamic sealing between the elongate rod and the plugged end of the indicator housing.

18. The indicator assembly as defined in claim 13, further comprising:

the litmus indicator including an elongate exterior screen having litmus granules therein.

19. The indicator assembly as defined in claim 13, wherein the lower end of the indicator housing includes threads for threaded engagement with a threaded aperture within a wall of the container.

20. The indicator assembly as defined in claim 13, wherein the lower end of the indicator housing further comprises:

a threaded fitting having external threads for threaded engagement with a threaded aperture within a wall of the container, the threaded fitting having said passageway therethrough for maintaining fluid communication between the interior of the container and the housing chamber.

* * * * *